United States Patent [19]

Menkis et al.

[11] Patent Number: 5,728,153
[45] Date of Patent: Mar. 17, 1998

[54] STENTLESS HEART VALVE SURGICAL SUPPORT DEVICE

[75] Inventors: Alan Menkis; Michael Scott, both of London, Canada; Ivan Vesely, Cleveland, Ohio

[73] Assignee: London Health Sciences Centre, London, Canada

[21] Appl. No.: 649,713
[22] PCT Filed: Nov. 23, 1994
[86] PCT No.: PCT/CA94/00647
    § 371 Date: Aug. 22, 1996
    § 102(e) Date: Aug. 22, 1996
[87] PCT Pub. No.: WO95/14443
    PCT Pub. Date: Jun. 1, 1995

[30] Foreign Application Priority Data

Nov. 24, 1993 [GB] United Kingdom ............... 9324201

[51] Int. Cl.⁶ ........................................ A61F 2/24
[52] U.S. Cl. ........................... 623/2; 606/139
[58] Field of Search .................. 606/151, 148; 623/2

[56] References Cited

U.S. PATENT DOCUMENTS

| | | | |
|---|---|---|---|
| 4,702,250 | 10/1987 | Ovil et al. | 128/334 |
| 5,053,043 | 10/1991 | Gottesman et al. | 606/148 |
| 5,197,979 | 3/1993 | Quintero et al. | 623/2 |
| 5,236,450 | 8/1993 | Scott | 623/2 |

*Primary Examiner*—Gary Jackson
*Attorney, Agent, or Firm*—Larkin, Hoffman, Daly & Lindgren, Ltd.; Sim & McBurney

[57] ABSTRACT

A reusable surgical device for holding a stentless valve during implantation. The surgical device has a generally cylindrical body mountable on a disposable, elongated handle. The generally cylindrical body defines a reduced diameter at one end for receiving the stentless valve thereon and permitting maneuvering space during suturing. A plurality of radial marking lines spaced approximately 120° apart indicated suture placement. Annular ridges form a groove permitting the stentless valve to be secured in place by a pressure-exerting fastener such as a tie wrap. The cylindrical body is inserted through the stentless valve with the marking lines oriented in predetermined relation to the valve leaflets until the stentless valve is properly positioned on the body, and the disposable handle is attached to the body.

21 Claims, 2 Drawing Sheets

STENTLESS HEART VALVE SURGICAL SUPPORT DEVICE

FIELD OF THE INVENTION

This invention relates in general to surgical devices, and more particularly to a stentless heart valve surgical support device.

BACKGROUND OF THE INVENTION

Heart valve disfunction can usually be corrected with surgery, involving repair or replacement of the diseased valves. The very best replacement for such a valve is a homograph, which is another human valve. Nevertheless, the availability of these valves is limited, so generally two types of replacement valves are currently used; mechanical and bioprosthetic (i.e. tissue). Mechanical valves are typically composed of tough, rigid materials, and usually do not fail structurally. However, mechanical valves require that the patient receive chronic anticoagulation therapy. Bioprosthetic valves are structured of chemically preserved animal tissue, usually from porcine or bovine sources. Tissue valves, because of their soft tissue composition, do not require chronic anticoagulation therapy. However, the tissue valves deteriorate in a similar manner to the patient's original valve, such that the survival rate is approximately 95% at five years, but only 40% at 15 years. Failure of the valve is usually a result of inadequate mechanical durability, atypical loading conditions and calcification.

Currently, bioprosthetic valve leaflets are made of tanned porcine aortic valves or calf pericardium, mounted on a rigid or pliable frame (also known as a stent). The purpose of the stent is to make it easier for the surgeon to implant the valve, since it allows the valve to retain its shape during surgery. Recently, using pathological and engineering analysis methods, it has been determined that the rigid stents themselves change the way in which the leaflets deform and carry load. To alleviate this problem, some valve manufacturers have begun producing stentless bioprosthetic valves. The lack of a stent and rigid cloth-covered ring, however, makes implantation of stentless valves difficult and time consuming. Several assistants are usually needed to hold the stentless valve in position with sutures and/or forceps or haemostats. This procedure is awkward for both the assistants and the surgeon performing the suturing. It is clearly advantageous to perform the valve surgery as quickly as possible, in order to ensure patient survival and rapid recovery.

To this end, at least one prior art holding device is known to facilitate surgical implantation of a heart valve. A stentless heart valve and holder is described in U.S. Pat. No. 5,197,979. This stentless heart valve holder is disposable and is detachably affixed to a suturable covering on the aortic segment of a heart valve, preferably via sutures which pass through holes in the holder.

However, this prior art holder suffers from the disadvantage that it cannot be thoroughly cleaned after use, due to the inclusion of internal threads for attaching a handle portion of the holder to a main body portion thereof. A further disadvantage of this prior art holder is that the holder is affixed to the valve via sutures, which necessitates time consuming connection. The prior art also does not provide space between the valve and holder for suturing of the valve to the patient's heart.

SUMMARY OF THE INVENTION

According to the present invention, a holding device for stentless valves is provided that allows accurate and easy positioning of the valve and facilitates suturing by adding rigidity to the valve structure. By utilizing the valve holding device of the present invention, surgery is made less complicated and faster.

Unlike U.S. Pat. No. '979, the valve holding device of the present invention is reusable with the exception of a detachable handle. A further advantage of the present invention is that it does not require the aortic segment of the valve to be enclosed by a suturable covering, as required in the prior art '979 patent. The present invention is not attached via sutures, but rather is preferably affixed by a tie wrap being wound around the valve. Furthermore, according to an aspect of the present invention markings are provided on the valve holder for indicating to the surgeon where sutures should be placed to ensure symmetrical suturing and accurate placement of the prosthesis into proper position.

BRIEF DESCRIPTION OF THE DRAWINGS

A preferred embodiment of the invention is described hereinbelow with reference to the following drawings, in which.

DETAILED DESCRIPTION OF THE PREFERRED EMBODIMENT

Figure 1:
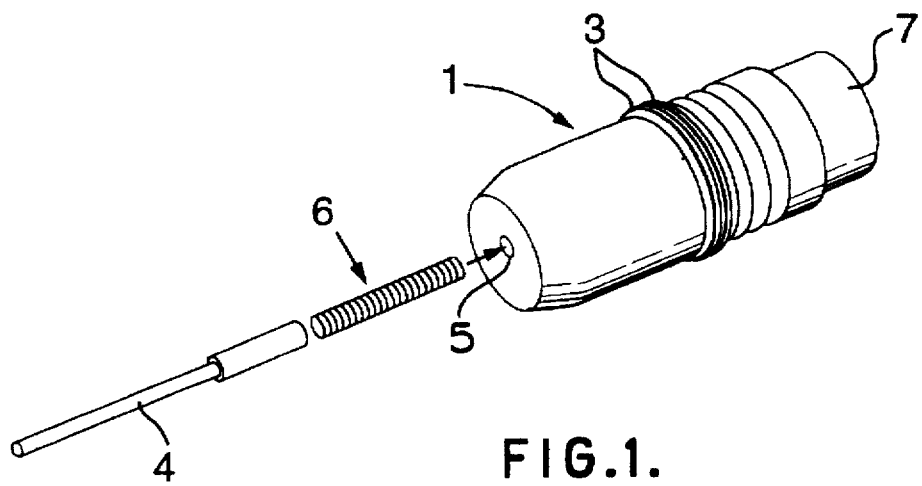
FIG. 1 is a perspective view of the stentless heart valve holder according to the present invention.

Turning to the drawings, the stentless heart valve holder of the present invention is shown comprising a generally cylindrical body 1 having a pair of annular ridges 3 circumscribing the centre thereof. At one end of the holder, a threaded hole 5 is provided for attachment to an approximately 1" rod 6, or other fastener, to which a handle 4 is attached. At an opposite end of the holder, a reduced diameter portion 7 is provided, the purpose of which is explained in greater detail below.

Various sizes of the valve may be accommodated by using different diameters and lengths of holder. With reference to FIG. 4, the diameter is denoted as $\varnothing$, while in FIG. 3, the length of the holder is given by $46.5 \text{ mm} + \delta$, where $\varnothing$ and $\delta$ are given in Table A, below, for different valve sizes (all dimensions being expressed in millimeters)

TABLE A

| VALVE SIZE | $\varnothing$ | $\delta$ |
| --- | --- | --- |
| 19 | 15 | 3 |
| 21 | 17 | 3.5 |
| 23 | 19 | 4.5 |
| 25 | 21 | 6 |
| 27 | 23 | 7.5 |

Figure 3:
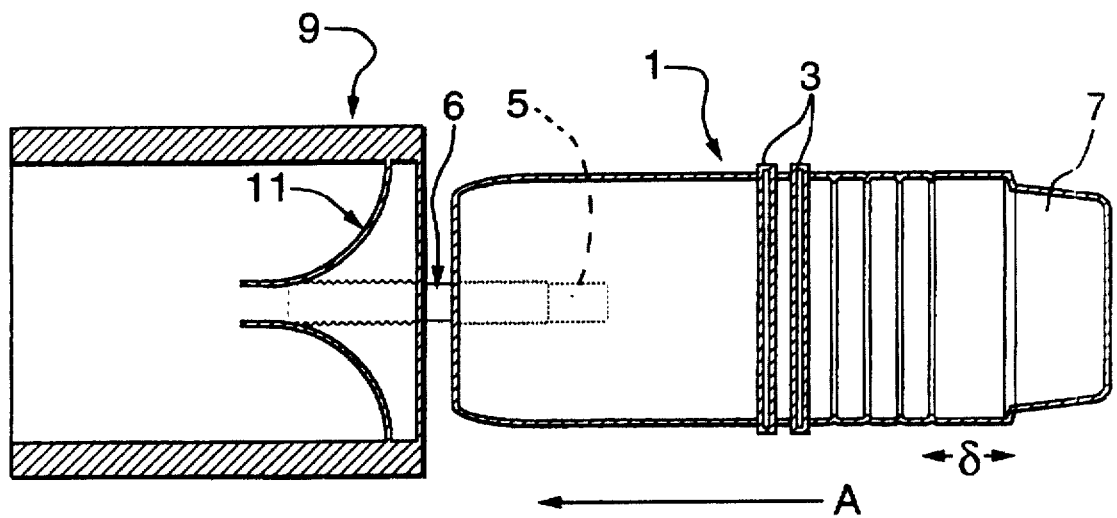
FIG. 3 shows insertion of the valve holder into a bioprosthetic heart valve.
Figure 4:
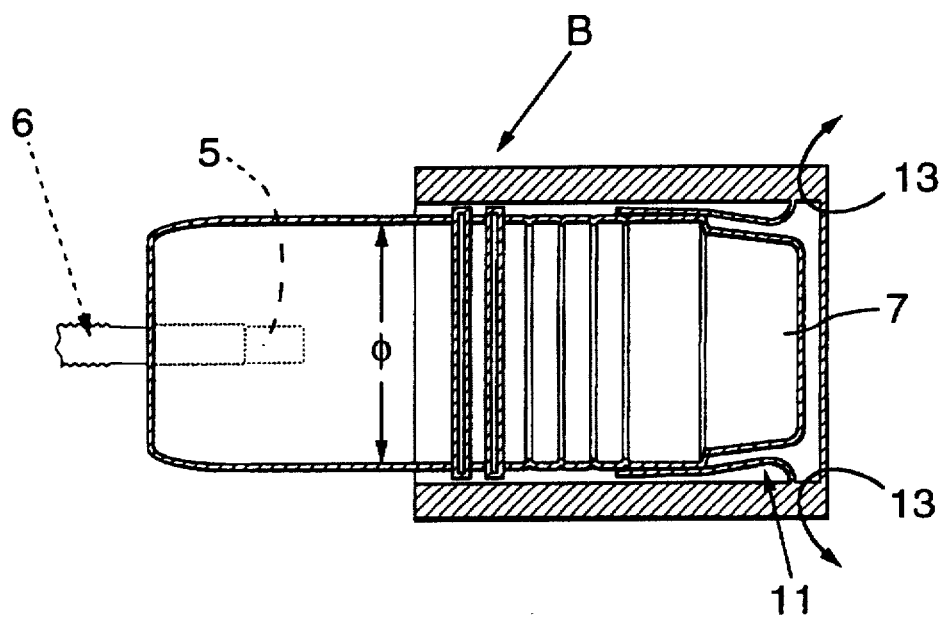
FIG. 4 shows the heart valve holder of the present invention in place within a bioprosthetic valve during surgical installation.

Turning to FIGS. 3 and 4, a bioprosthetic valve 9 is shown which comprises the aortic root of a pig or other animal. The valve is generally cylindrical having three bioprosthetic leaflets 11 adjacent one end thereof.

In operation, the valve holder of the present invention is inserted into the valve 9 in the direction of arrow A (FIG. 3).

As the valve holder is inserted into the valve, the leaflets 11 are gently pushed backwards. The holder is advanced into the valve 9 so as to form a friction fit therewith. Once the holder has been inserted into the valve to the position shown in FIG. 4, the handle 4 (FIG. 1) is attached to the rod 6. Next, a tie wrap (not shown) is wound around the valve at the location identified as B in FIG. 4, which is intermediate the pair of annular ridges 3. By tieing the plastic wrap around the upper end of the valve 9 so as to compress and squish the portion B of the valve into the groove between ridges 3, a snug and secure connection is effected between the holder and the valve 9. Alternative embodiments of the invention are contemplated which would allow the prosthesis to be clipped onto the holder with spring loaded clips or with a metallic snap ring.

Figure 5:
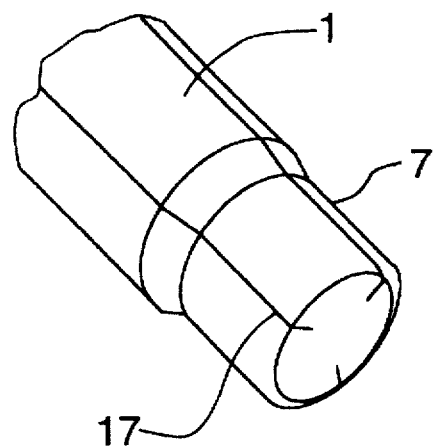
FIG. 5 is an end view of the heart valve holder according to the preferred embodiment showing markings for suture placement.

As shown in FIG. 4, the leaflets 11 are bent backward into the valve 9. The reduced diameter portion 7 results in a clearance between the leaflets 11 and the valve holder which provides adequate maneuvering room for the surgeon to apply sutures 13. FIG. 5 demonstrates that markings 17 are provided on the holder for indicating to the surgeon where sutures should be placed in order to ensure proper positioning of the valve in the recipient aortic root and to minimize leakage. These alignment markers may be engraved on the reduced diameter portion 7 at 120 degrees apart.

During suturing of the valve into the patient's heart, the valve holder ensures that the valve does not collapse in response to tugging or pulling at the top and bottom ends of the valve. Once the valve has been installed, the holder may be removed by releasing the tie wrap or cutting the valve below the tie wrap, and pulling out the holder via the handle 4 attached to rod 6. The handle 4 attached to rod 6 is made via injection molding, and it is contemplated that the handle will be disposed of after each operation and a new handle 4 used for each subsequent surgical operation. The valve holder itself may be cleaned and sterilized for repeated use. The short rod 6 remains affixed to the holder 1 and can be easily cleaned since the threads are exposed. The handle 4 is disposed of after each operation because the threaded hole which connects to rod 6 cannot be easily cleaned.

Figure 2:
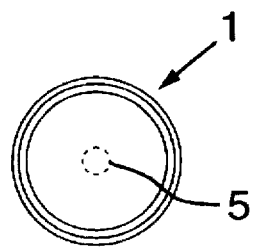
FIG. 2 is an end view of the valve holder of FIG. 1.

According to one method of fabricating the holder of the present invention, the devices may be machined on a lathe from cylindrical acrylic or polycarbonate, and then sanded and polished. According to the best mode of the invention at the time of filing this application, the machining process is as follows:

1. Rough cut a length of acrylic (or polycarbonate).
2. Remove extra material by turning down to almost final diameter.
3. Contour holder according to FIGS. 1, 2 and 3.
4. Bore tap hole 5 for mounting handle.
5. Sand with wet/dry sand paper using 320, 400 then 600 grit (begin with 240 grit if necessary).
6. Polish with a polishing compound such as Autosol(c) ™.
7. Tap hole 5 for threaded rod 6.
8. Scribe commissural lines 17 at 120°
9. Clean and spot polish if necessary.
10. Apply glue to rod 6 and insert into hole 5.

Acrylic or polycarbonate in cylindrical sections have been identified as desirable materials because of their durability, lightness, transparency and ease of sterilization. It is contemplated that raw sections should be used which are only slightly larger than final dimensions in order to minimize waste. The machining method for producing the device according to the present invention requires only a lathe, cutters, tap drill bit and tap. A numerically controlled lathe may be used for larger scale production.

If demand for the device according to the present invention is sufficient, it is also contemplated that injection molding of the device would be possible.

In summary, surgeons currently use sutures, forceps and/or haemostats to position and hold the prosthesis during suturing. Because the valve is very pliable and the aortic wall of the valve is tough, suturing is difficult. Usually, an assistant is required to hold positioning (alignment) sutures while the attachment is completed. The valve holder of the present invention eliminates the need for positioning sutures, and eases the suturing process. The valve holder itself is attached to the valve by a tie wrap which fits snugly into a groove in the valve rather than by sutures. The device increases the rigidity of the aortic root during surgery, resulting in easier suturing. In addition, the reduced diameter of the valve holder at the suturing end provides maneuvering room for a surgeon to apply the sutures. Furthermore, according to the embodiment of FIG. 5, markings 17 are provided on the holder for indicating to the surgeon where sutures should be placed in order to ensure proper positioning of the valve in the recipient root. The holder of the present invention replaces conventional tools while providing more positive control over the position of the prosthesis. This holder is also economical since it is reusable with the exception of the detachable handle.

The present invention is not limited to the features of the embodiments described herein, but includes all variations and modifications within the scope of the claims.

The embodiments of the invention in which an exclusive property or privilege is claimed are defined as follows:

1. A surgical device for holding a stentless valve for use with a disposable handle, said surgical device comprising:
   a generally cylindrical body having a first end, a second end having a reduced diameter relative to said first end, a mounting member disposed adjacent the first end for detachably mounting the generally cylindrical body to the disposable handle.

2. The surgical device of claim 1 wherein the generally cylindrical body has a central region and the surgical device further comprises:
   at least two annular ridges circumscribing the central region.

3. The surgical device of claim 2 wherein the annular ridges are spaced a predetermined distance apart to form a groove such that a secure connection of the valve to the surgical device is effected when pressure is exerted around the stentless valve so as to squeeze a portion of the stentless valve into the groove.

4. The surgical device of claim 1 wherein the valve is implanted using sutures, and wherein the second end of the generally cylindrical body includes marking lines disposed radially thereabout to indicate where the sutures should be applied to the stentless valve.

5. The surgical device of claim 4 wherein the marking lines are spaced approximately 120 degrees apart.

6. The surgical device of claim 1 wherein the reduced diameter of the second end of the cylindrical body is gradually reduced to a diameter which provides maneuvering space between the stentless valve and the second end of the cylindrical body for suturing during surgery.

7. The surgical device of claim 1 wherein the disposable handle is internally threaded and the mounting member is a rod extending from the generally cylindrical body having an outside surface threaded for mating connection to the disposable handle.

8. The surgical device of claim 1 fabricated from a material selected from the group consisting of acrylic and polycarbonate.

9. The surgical device of claim 1 wherein the generally cylindrical body is reusable.

10. A surgical device for holding a stentless valve during implantation, said surgical device comprising:

a generally cylindrical body having a first end, a second end, and a mounting member disposed adjacent said first end, said second end having a reduced diameter relative to said first end; and a disposable handle mountable on said mounting member.

11. The surgical device of claim 10 wherein the generally cylindrical body has a central region and the surgical device further comprises:

at least two annular ridges circumscribing the central region.

12. The surgical device of claim 11 wherein the annular ridges are spaced a predetermined distance apart to form a groove such that a secure connection of the valve to the surgical device is effected when pressure is exerted around the stentless valve so as to squeeze a portion of the stentless valve into the groove.

13. The surgical device of claim 10 wherein the valve is implanted using sutures, and wherein the second end of the generally cylindrical body includes marking lines disposed radially thereabout to indicate where the sutures should be applied to the stentless valve.

14. The surgical device of claim 13 wherein the marking lines are spaced approximately 120 degrees apart.

15. The surgical device of claim 10 wherein the reduced diameter of the second end of the cylindrical body provides maneuvering space between the stentless valve and the second end of the cylindrical body for suturing during surgery.

16. The surgical device of claim 10 wherein the disposable handle is internally threaded, and the mounting member has an outside, said outside being threaded for mating connection to the disposable handle.

17. The surgical device of claim 10 fabricated from a material selected from the group consisting of: acrylic and polycarbonate.

18. The surgical device of claim 10 wherein the generally cylindrical body is reusable.

19. A method for mounting a stentless valve for implantation, said method comprising the steps of:

providing a handle and a surgical device for holding the stentless valve, said surgical device including a generally cylindrical body having a first end, a second end, and a mounting member disposed adjacent said first end, said second end having a reduced diameter relative to said first end;

disposing the stentless valve on said surgical device by passing said first end of said surgical device through the stentless valve such that at least a portion of said surgical device remains within the stentless valve; and mounting the handle on the first end of the surgical device.

20. The method of claim 19 further comprising the steps of:

removing the surgical device from the stentless valve subsequent to implantation;

dismounting the handle from the surgical device; and reusing the surgical device to implant a like stentless valve.

21. The method of claim 19 wherein the step of providing the surgical device includes providing the surgical device with a pair of annular ridges circumscribing a central region of the generally cylindrical body and defining a groove therebetween, the method further comprising the step of:

exerting pressure around the stentless valve so as to squeeze a portion of the stentless valve into the groove between the annular ridges so as to secure the stentless valve to the surgical device.

\* \* \* \* \*